(12) United States Patent
Boate et al.

(10) Patent No.: US 8,882,272 B2
(45) Date of Patent: Nov. 11, 2014

(54) METHOD AND APPARATUS FOR IMAGING THE CHOROID

(75) Inventors: Alan Boate, Ottawa (CA); Jeremy Lloyd Gribben, Ottawa (CA); David Alexander Kahn, Ottawa (CA)

(73) Assignee: Annidis Health Systems Corp., Ottawa, Ontario (CA)

( * ) Notice: Subject to any disclaimer, the term of this patent is extended or adjusted under 35 U.S.C. 154(b) by 0 days.

(21) Appl. No.: 13/806,335

(22) PCT Filed: Jun. 23, 2011

(86) PCT No.: PCT/CA2011/050389
§ 371 (c)(1),
(2), (4) Date: Dec. 21, 2012

(87) PCT Pub. No.: WO2011/160238
PCT Pub. Date: Dec. 29, 2011

(65) Prior Publication Data
US 2013/0107211 A1    May 2, 2013

Related U.S. Application Data

(60) Provisional application No. 61/358,683, filed on Jun. 25, 2010.

(51) Int. Cl.
*A61B 3/14* (2006.01)
*A61B 3/10* (2006.01)
*A61B 3/00* (2006.01)
*A61B 3/12* (2006.01)

(52) U.S. Cl.
CPC ............. *A61B 3/0008* (2013.01); *A61B 3/1241* (2013.01); *A61B 3/14* (2013.01)
USPC ............ 351/206; 351/205; 351/210; 351/221

(58) Field of Classification Search
USPC ......... 351/206, 213, 200, 205, 210, 209, 221, 351/222, 223, 246
See application file for complete search history.

(56) References Cited

U.S. PATENT DOCUMENTS

| | | | | |
|---|---|---|---|---|
| 6,494,576 | B1 * | 12/2002 | L'Esperance, Jr. | 351/206 |
| 2004/0075812 | A1 * | 4/2004 | Kardon et al. | 351/206 |
| 2004/0142485 | A1 * | 7/2004 | Flower et al. | 436/172 |
| 2007/0159600 | A1 | 7/2007 | Gil et al. | |
| 2009/0153797 | A1 * | 6/2009 | Allon et al. | 351/206 |

FOREIGN PATENT DOCUMENTS

WO    2006/119349    11/2006

OTHER PUBLICATIONS

Cohen et al., "Biomicroscopial Choroidoscopy (Uveoscopy) and Transillumination Gonioscopy", Arch Ophthalmol, vol. 94, Sep. 1976, pp. 1618-1621.
Cohen et al., "Choroidograhy and Photography of the Long Ciliary Nerve and Artery", Arch Ophthalmol, vol. 95, Mar. 1977, pp. 436-437.
International Patent Application No. PCT/CA2011/050389, International Search Report dated Aug. 19, 2011.
Canadian Patent Application No. 2,840,124, Office Action dated Mar. 6, 2014.

* cited by examiner

*Primary Examiner* — Dawayne A Pinkney
(74) *Attorney, Agent, or Firm* — Mukundan Chakrapani; Borden Ladner Gervais LLP

(57) ABSTRACT

A method and apparatus for imaging the choroid. The method comprises indirectly illuminating the choroid of an eye using incident light having a wavelength spectrum in the near-infrared region; and collecting the light passing out through the choroid and the pupil of the eye using an image sensor to obtain an image of the choroid.

17 Claims, 5 Drawing Sheets

TYPICAL LIGHT PATHS WITHIN THE SCLERA

TYPICAL LIGHT PATHS WITHIN THE SCLERA

POLAR DIAGRAM OF SCLERAL SCATTERING

ILLUMINATION AND COLLECTION ARRANGEMENT (SIDEVIEW)

METHOD AND APPARATUS FOR IMAGING THE CHOROID

FIELD

The present disclosure relates generally to a method and apparatus for imaging an eye. More particularly, the present disclosure relates to a method and apparatus for imaging the choroid.

BACKGROUND

The use of fundus imagers and ophthalmoscopes is well established as a means to non-invasively examine the retina of the human eye to aid in the detection and nature of ocular diseases. Such instruments inject light through the pupil of the eye and collect light reflected from the retina and passing back through the pupil.

This type of observation is well suited for the examination of the upper layers of the retina and routinely shows a bright optical nerve head (ONH) and blood vessels leading back to the ONH.

The layer below the retina, the choroid, remains substantially hidden from such observations because most of the incident light is reflected or absorbed before it reaches the choroidal layer. The choroid, also known as the choroidea or choroid coat, is a vascular layer containing connective tissue of the eye lying between the retina and the sclera, as shown in FIG. 1. In humans the thickness of the choroid is about 0.5 mm. The choroid provides oxygen and nourishment to the outer layers of the retina.

Non-invasive observation of the choroid can provide useful and significant information pertaining to a number of ocular diseases, such as choroidal melanoma and choroidal neovascularisation.

SUMMARY

A method and apparatus for imaging the choroid is disclosed.

In a first aspect, the present disclosure provides a method for imaging the choroid. The method comprises indirectly illuminating the choroid of an eye using incident light having a wavelength spectrum in the near-infrared region and collecting the light passing out through the choroid and the pupil of the eye using an image sensor to obtain an image of the choroid.

In a further aspect, there is provided an apparatus for imaging the choroid. The apparatus comprises an illumination source and an image sensor. The illumination source indirectly illuminates the choroid of an eye using incident light having a wavelength spectrum in the near-infrared region. The image sensor collects the light passing out through the choroid and the pupil of the eye to obtain an image of the choroid.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures, in which.

DETAILED DESCRIPTION

Generally, the present disclosure provides a method and apparatus for imaging the choroid.

In various example embodiments the following features may be included collectively or alone or in any combination thereof.

Figure 8:
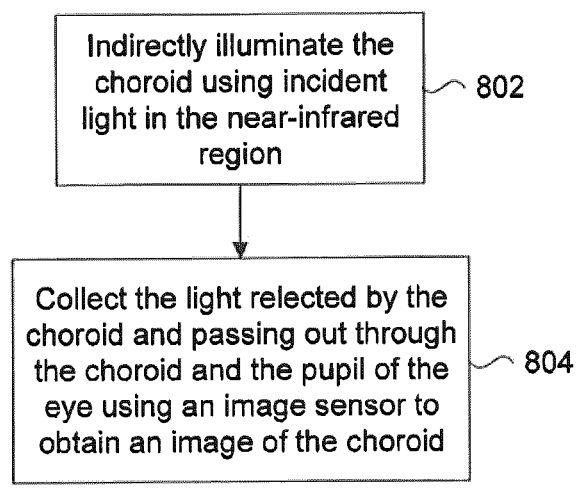
FIG. 8 is a flow chart illustrating a method of imaging the choroid in accordance with an embodiment.

The present disclosure provides a method for imaging the choroid as shown in FIG. 8. The method comprises indirectly illuminating the choroid of an eye using incident light having a wavelength spectrum in the near-infrared region (802) and collecting the light passing out through the choroid and the pupil of the eye using an image sensor to obtain an image of the choroid (804).

The indirect illumination of the choroid may be accomplished by transclerally illuminating the choroid. Transcleral illumination of the choroid may comprise applying the incident light transdermally through the upper or lower eyelid. Indirect illuminating the choroid may comprise propagating a substantial portion of the incident light through the sclera of the eye, where the sclera acts as a waveguide to guide the incident light to the choroid. Indirectly illumination of the choroid may comprise illuminating the choroid by applying incident light at a plurality of locations surrounding the eye using one or more light sources associated with different angles of incidence. The proportion of the incident light that propagates through the sclera to the rear of the eye to the incident light that is transmitted through the sclera near the front of the eye may be controlled.

The image of the choroid may be obtained by capturing a single image of the choroid or by capturing a continuous stream of images of the choroid. The captured image or stream may include an image of the Haller or Sattler layers of larger choroidal vessels.

An additional light source having a wavelength spectrum in the visible region may be provided for identifying the illumination region of the incident light having the wavelength spectrum in the near-infrared region.

At least one of size, shape, orientation and convergence angle of the incident light may be adjusted to minimize interference from unwanted scattering.

Blood oxygenation level may measured using at least two images obtained at different wavelengths on either side of the oxygen isobestic wavelength in the near-infrared region.

The present disclosure also provides an apparatus for imaging the choroid. The apparatus comprises an illumination source and an image sensor. The illumination source indirectly illuminates the choroid of an eye using incident light having a wavelength spectrum in the near-infrared region. The image sensor collects the light passing out through the choroid and the pupil of the eye to obtain an image of the choroid.

The illumination source may include means to propagate a substantial portion of the incident light through the sclera of the eye for the indirect illumination of the choroid. In addition, the illumination source may include means to illuminate the choroid through a plurality of locations surrounding the eye. The illumination source may also include one or more light emitting diodes (LEDs) emitting light in one or more wavelengths in the near-infrared region. The illumination source may be a single discrete source, a distributed source or an aggregation of discrete sources.

The apparatus may further comprise means to capture a single image of the choroid or means to capture a continuous stream of images of the choroid.

The apparatus may further comprise an optical fibre to deliver the incident light having a wavelength spectrum in the near-infrared region.

The apparatus may further comprise an additional light source having a wavelength spectrum in the visible region for identifying the illumination region of the incident light having the wavelength spectrum in the near-infrared region.

In the following description, for purposes of explanation, numerous details are set forth in order to provide a thorough understanding of the embodiments. However, it will be apparent to one skilled in the art that these specific details are not required. In addition, it is understood that the features described with respect to any example embodiment can be included in other embodiments as well, where technically feasible as understood by a person skilled in the art.

As discussed earlier, the choroid is a layer in the vertebrate eye, which lies immediately outside the retina, between the retina and the sclera. The choroid contains blood vessels, which carry nourishment to the outer layers of the retina, and pigment. The choroid connects with the ciliary body toward the front of the eye and is attached to edges of the optic nerve at the back of the eye. The choroid consists of four layers: an outermost layer of large blood vessels (Haller's layer), a layer of intermediate size blood vessels (Settler's layer), a layer of capillaries (choriocapillary layer), and an innermost layer (Bruch's membrane). The ability to non-invasively image the choroid can provide a wealth of information pertaining to ocular health and can act as a diagnostic tool to detect and monitor various ocular diseases.

The method for imaging the choroid comprises indirectly illuminating the choroid of an eye using incident light having a wavelength spectrum in the near-infrared (NIR) region and collecting the light passing out through the pupil of the eye using an image sensor to obtain an image of the choroid. Indirect illumination of the choroid can include illuminating the choroid transclerally (i.e., via the sclera) either by directly illuminating the sclera or by illuminating the sclera transdermally (for example, through the skin surrounding the eye).

Several techniques have been attempted to illuminate the interior of the eye avoiding the use of the pupil as the route of illumination. Such techniques involve illuminating the interior of the eye through the white sclera layer that surrounds the eye. Prior attempts at illuminating the interior of the eye through the sclera involve the direct illumination of the sclera from the illumination source, usually a laser or an incandescent source, for example a tungsten filament. As the only part of the sclera that is readily accessible directly is that in the close neighborhood of the pupil, this limits the potential of the prior techniques. Moreover, the choice of white light as an illumination source resulted in substantial patient discomfort.

For example, Cohen et al in "Choroidography and Photography of the Long Ciliary Nerve and Artery" Arch Ophthalmol—Vol 95 March 1977, p 436, described an imaging technique using visible white light from a tungsten halogen source and capturing the images in a photographic film, such as Kodak TRI-X™, ASA 2000. The light from the lamp was introduced to the patient via a fibre optic cable, the far end of which was pressed against the patient. In this arrangement, the light passed to the choroid through a transcutaneous (transdermal) and transcleral pathway.

Other prior art systems illuminate the interior of the eye through the sclera without contacting the patient by focusing light on the sclera close to the eye. Such systems also describe the use of visible light for providing uniformity in the illumination of the retina. The illumination source is typically a lamp such as a xenon, halogen, or metal-halide lamp, or any other filament, arc or gas lamps and uses specific optical components to filter out ultraviolet and infrared components of the light used for illumination. As described earlier, use of white light as an illumination source not only results in substantial patient discomfort, but also may obscure otherwise pertinent information about ocular health.

Yet other prior art systems describe the use of fluorescent dyes injected into a patient's eye for imaging the choroid. The dyes result in the blood vessels and the optic nerve appearing as bright areas in the resultant images. However, injecting fluorescent dyes in patients raises the concern of an anaphylactic reaction in addition to usual substantial patient discomfort from the illuminating flash.

However, in accordance with example embodiments described herein, the choroid of the eye is indirectly illuminated using incident light having a wavelength spectrum in the NIR region. The light passing out through the pupil of the eye is collected using an image sensor to obtain an image of the choroid. The illumination, for example, may be made to pass through layers of skin forming the lower eyelid. In other example embodiments, illumination may be provided through the skin at either side of the eye and/or through the upper eyelid. In other example embodiments, illumination may be provided directly to the scleral surface. The use of fluorescent dyes is eliminated while patient comfort is sustained by the use of light in the NIR region, which is substantially invisible to the human eye.

In order to prevent excessive absorption of the illuminating light prior to entering the interior of the eye and to enable patient comfort, light from a spectral band in the NIR region of the spectrum is used. For example, the spectral band may lie in the region from 750 nm up to 1000 nm or longer. The transmission of infra red light through the skin, sclera and eye tissues improves as the wavelength increases. The upper limit on of the wavelength spectrum is influenced by the spectral sensing properties of the image sensor that is typically a silicon-based Charge Coupled Device (CCD) or a Complementary Metal Oxide Silicon (CMOS) device, both of which have very low sensitivity above 1000 nm. However, the emerging technology of image sensors that operate at longer wavelengths such as those based on InGaAs technology would enable imaging at longer wavelengths.

In preliminary trials, light emitting diode (LED) sources operating at a nominal centre wavelength of 890 nm have yielded good quality images of the choroid. Good quality images have been similarly achieved at 940 nm. In both cases, the LED used provides light that is partially collimated to present a full cone angle of divergence of about 40 degrees. The LEDs used have an industry standard 5 mm lensed package.

As light at the NIR region of the spectrum is substantially invisible, some light in the visible region of the spectrum may be provided to allow the operator to view the point of illumination during alignment. The visible light may be turned off prior to image capture in order to prevent unwanted interference.

In some embodiments, the illuminating light can be delivered to the sclera indirectly with or without contact of the illumination source to the skin or sclera, and with or without a flexible light guide that delivers the incident light. Once the incident light is redistributed within the sclera and re-radiated from the rear of the choroid, the redirected light passing out through the pupil is collected and is then relayed to a focus at the image sensor where the choroid layer is in focus.

Figure 1:
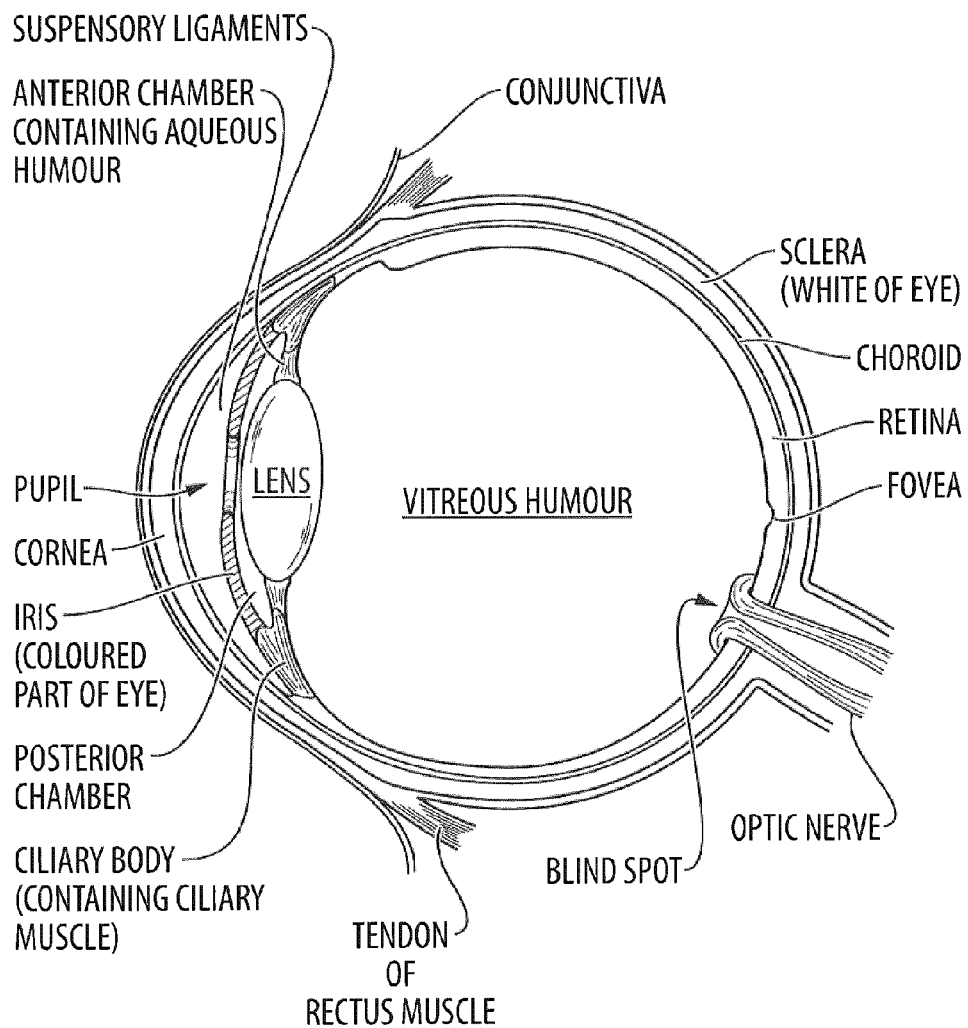
FIG. 1 is a cross-sectional side view of an eye.
Figure 2:
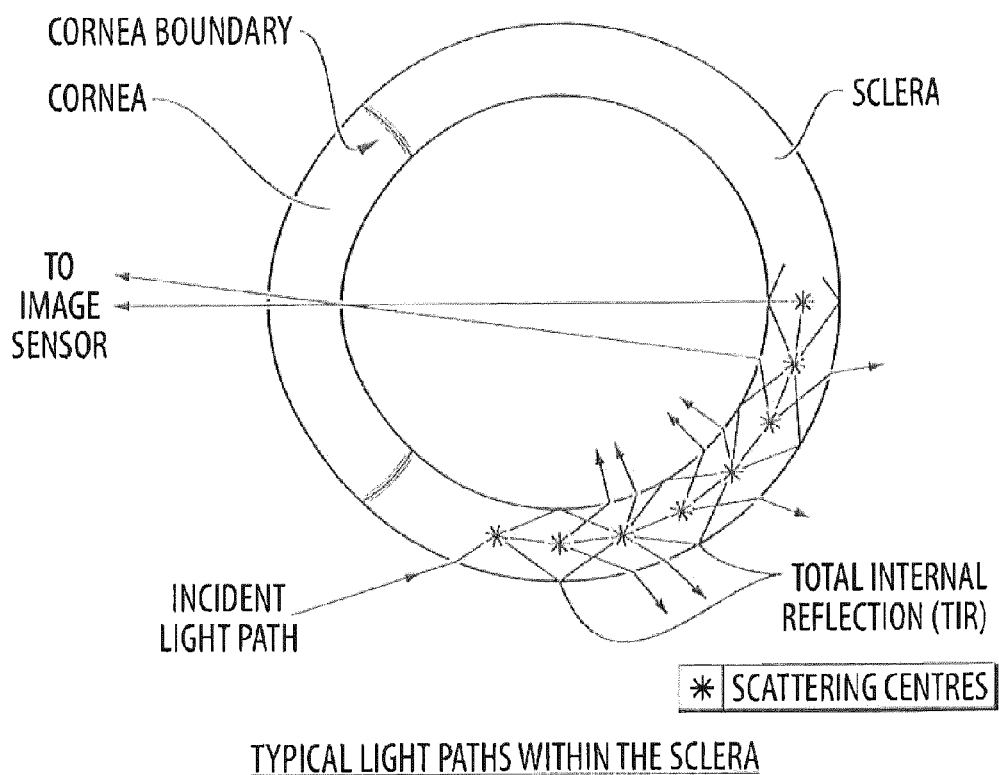
FIG. 2 is a cross-section of the sclera and the cornea showing typical light paths in accordance with an embodiment.

It would appear that the light entering the sclera is partially scattered and then partially guided through the sclera towards the back of the eye and that the sclera is acting as a lossy waveguide layer redistributing the light to an area different from where it is captured, as shown in FIG. 2. Such a waveguide property is consistent with the structure of the sclera which is made up irregular collagen fibres that are continuous with the cornea and reach around to the back of the retina, as shown in FIG. 1. The refractive index of the collagen fibres of the sclera is about 1.45. The refractive index of the surrounding tissues is near 1.33. Light propagating within the sclera in a direction far away from the normal to the sclera will be totally internally reflected within the sclera provided the angle of propagation with respect to the local scleral plane is less than the limiting angle. In a step index structure, the angle is given by $\cos^{-1}(n2/n1)$ where $n1$, $n2$ are the respective refractive indices. However, the sclera has more of a graded structure. Some portion of the light will also be internally scattered as it propagates within the sclera, and some of the scattered light will be at angles greater than the limiting angle—this portion of the light will pass through the sclera and back-illuminate the choroid. The sclera absorbs less and scatters less with the longer wavelengths used in the IR part of the spectrum than it would in the visible region of the spectrum. In order to channel the incident light into the sclera such that the sclera acts as a waveguide, the location and angle of the launching of incident or illuminating light become important as discussed below.

The optical properties of the sclera change significantly and monotonically as the wavelength increases from the visible region into the NIR region of the spectrum. In particular, the absorption reduces and the scattering reduces, the respective coefficients typically falling by over 50%. Moreover, the relative proportion of forward scattering to backscattering increases. Thus, using illuminating light in the NIR allows more light to pass into and through the sclera, especially where the light path is substantially close to the local plane of the sclera where the sclera is acting as a waveguide or a lightguide.

FIG. 2 shows a cross-section of the sclera and the cornea showing typical light paths when illuminated in accordance with embodiments described herein. FIG. 2 additionally shows the phenomena of refraction, total internal reflection, and scattering as well as the light path out through the cornea to the image sensor.

As described earlier, the sclera is a connective tissue made mostly of white collagen fibres. It underlies the choroid posteriorly and continues anteriorly where it becomes transparent over the iris and pupil and is referred to as the cornea, as shown in FIG. 1. Light incident upon the exterior surface of the cornea travels through the cornea and exits the other surface and no light gets trapped within the cornea.

In contrast, light incident, directly or indirectly upon the exterior surface of the sclera is scattered in all directions. A portion of the incident light proceeds through the inner surface of the sclera and the remaining portion of the incident light is scattered at an angle consistent with the waveguide properties of the sclera and is, therefore, trapped within the sclera. Another portion of the incident light is backscattered and lost.

The trapped light will however itself be continuously scattered. As a result, a portion of the incident light passes through the inner surface while the remainder remains trapped and will be partially scattered out further along. The overall effect is that the entire sclera acts as a distributed secondary source of light or illumination, including part of the sclera at the back of the eye remote from the initial point of entry of the incident light.

Figure 3:
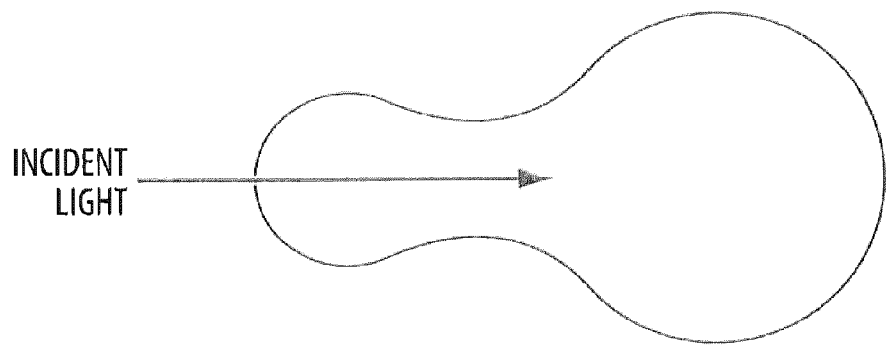
FIG. 3 is a typical polar diagram of a scattering medium showing a preference for forward scattering over backward scattering.

Scattering in the NIR is generally not isotropic, but has a characteristic polar pattern with preferred axes in the forward and rearward directions, especially in the forward direction as shown in FIG. 3.

In order to optimally launch light into the scleral waveguide, the incident light should not impact the sclera at right angles but instead impact the sclera at angles close to the plane of the sclera at the point of illumination. The optimal launch angle for the illuminating incident light can be achieved by choosing a suitable location to launch the light and by directing the light in a preferred limited range of angles extending over typically plus and minus 10 degrees around the central axis of propagation. The size and shape of the illuminated region on the skin, and the associated convergence angle and orientation of the incident light are determining parameters of the choroidal illumination. These geometric parameters can be optimized to minimize interference from unwanted scattering thereby improving the quality of the resulting image. The required beam parameters may be set by, for example, suitable combinations of lenses and apertures. The use of fibre optic cable as a convenient transport element for the illuminating light allows for flexibility of deployment, and can serve to more evenly distribute the modes within a set mode volume.

The mode volume of a light beam, sometimes called the optical throughput, or etendue, is the product of near-field focused area and far-field solid angle. When divided by the square of the wavelength, the result is the number of fundamental geometric modes. In indirectly illuminating the choroid through the sclera, an objective is to maximize the proportion of incident light that is converted by internal scattering into modes that are guided within the sclera around to the rear of the eye. If the incident light is near normal to the scleral surface, most of the energy will be forward scattered right through the sclera or backscattered from the sclera. Therefore, it is desirable to illuminate employing an incident angle that is far from normal. It is also desirable to use a mode volume that is highly collimated, that is where the spread of angles is small, subject only to the need to allow for some tolerancing in the alignment. The shape of the illuminated area may be circular or square or in the form of a partial annulus, or in any intermediate shape. The size of the illuminated area can be limited so to allow the incident angles at the scleral surface to be substantially similar; typically, this implies an illumination shape limited in the vertical direction to approximately 1 or 2 millimeters. The partial annulus however could usefully extend approximately horizontally by several more millimeters. The size of the human eyeball is remarkably consistent and the precise location for illumination can use as a reference point the pupil of the eye when the eye is fixated upon a target.

In an example embodiment, the optical fibre has a core diameter of approximately 5 mm and is connect firstly to a collection lens and secondly to a focusing lens. As described earlier, the fibre allows for easy flexibility during deployment and also tends to mix the rays and for facilitating an even level of illumination. However, other combinations of optical elements can be used to accurately define the illuminating beam in terms of shape, size, incident angle and convergence.

Figures 4, 5:
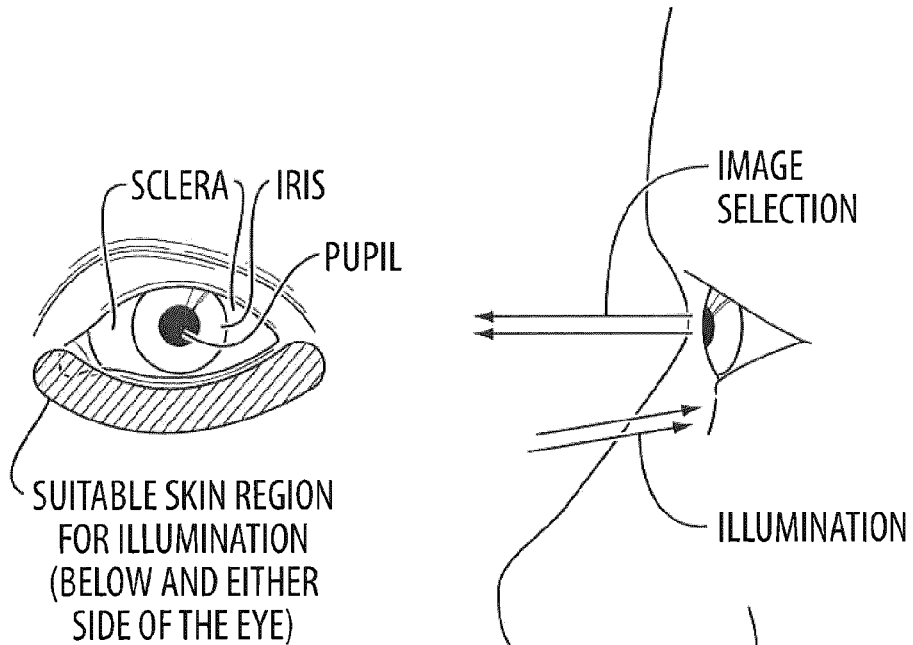
FIG. 4 is a front view of the eye and surrounding skin below illustrating regions for injecting light for imaging the choroid in accordance with an embodiment.
FIG. 5 is a side view of a face showing light launched below the eye (or towards the edge) and the light passing out through the pupil for imaging the choroid in accordance with an embodiment.

FIG. 4 is a front view of the eye and surrounding skin below illustrating regions for injecting light for imaging the choroid in accordance with an embodiment. FIG. 5 is a side view of a face showing light launched below the eye (or towards the edge) and the light passing out through the pupil for imaging the choroid in accordance with an embodiment.

An advantage of the indirect illumination of the choroid is that there is no reflection of illumination from the cornea or the viewing lens, nor is there backscattering from other regions of eye tissue beyond the cornea. This avoids the need to block or remove the otherwise dominant corneal reflection and facilitates the capture of good quality images.

Figure 6:
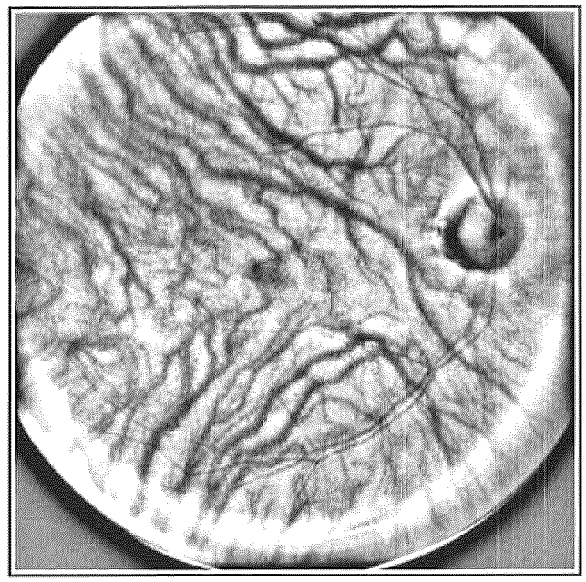
FIG. 6 is an image of the choroid obtained from illumination of the choroid from light injection through the lower eyelid.

The nature of the images so obtained depends on the illumination geometry. In one form of illumination, light injected or launched through the lower eyelid enters the sclera and appears to provide illumination from the back of the eye beyond the retina. As in the example shown in FIG. 6, images obtained with this type of illumination have the choroidal vessels appearing as dark areas, in effect shadowing the rear sourced illumination, while the other choroidal areas appear bright as they do not greatly attenuate the rear sourced illumination. Also, the dark appearance of the ONH may indicate that there is no part of the distributed scleral light illumination behind the ONH as the ONH physically disrupts the sclera. Moreover, the ONH is often apparently surrounded with a bright annulus, the overall appearance resembling a lunar eclipse of the sun.

While this form of illumination also shows in shadow form the arterioles and venules in front of the retina leading to the ONH, the predominant shadowed vessels are those of the choroid that do not originate at the ONH. In example embodiments, the images may be inverted in brightness, analogous to viewing a negative image, prior to presenting to physicians, who are more familiar with seeing bright vessels for diagnostic purposes.

Figure 7:
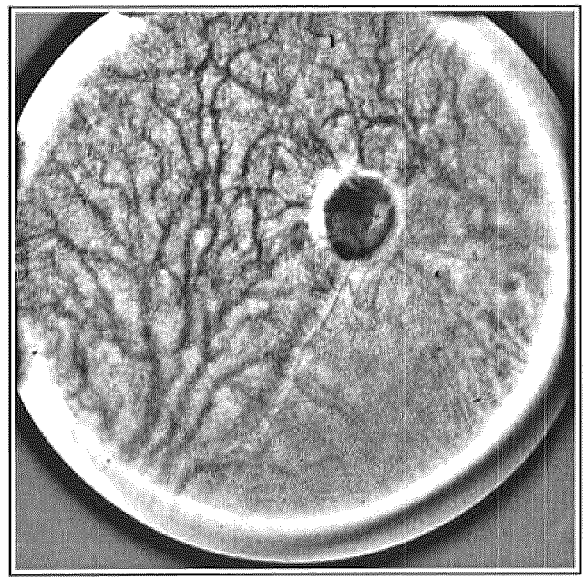
FIG. 7 is an image of the choroid obtained from illumination of the choroid from light injection through a different portion of the lower eyelid, where the upper left portion appears to be back lit, while the lower right portion appears front lit as in a conventional fundus image.

In other illumination arrangements, specifically where the light is arranged to initially illuminate a different part of the lower eyelid, the image shows a combination of both the shadow features described above and reflection features commonly associated with conventional front illumination, as shown in FIG. 7. This suggests that in the latter case, some of the light passes through the sclera near the front of the eye to provide front illumination, while some light travels around to the rear of the eye to provide rear illumination. The illumination through different parts or portions is associated with different angles of the light paths as they intersect with the sclera.

The light collected through the pupil at the image sensor may contain portions of light scattered from various paths of lesser interest in addition to the portion of particular interest scattered from the choroid. Consequently, the contrast ratio of the raw images may be poor. However, as the image is captured electronically and stored digitally, the images can be processed to enhance the contrast and emphasize the desired clarity of the image for diagnostic purposes. The ability to digitally enhance the contrast of the images obtained presents an advantage over prior art techniques that rely on photographic films and/or plates.

From the preliminary trials, it may be inferred that the angle of illumination and the region near the eye where the illumination occurs controls the proportion of light that propagates through the sclera to the rear of the eye to the light that is transmitted through the front of the eye before being reflected back passing out through the pupil to the collection optics. In some exemplary embodiments, the method for imaging the choroidal vessels may include adjusting the proportion of incident light that propagates through the sclera to the rear of the eye to incident light that is transmitted through the front of the eye.

The images may be captured individually or in a continuous stream in a video format. For clinical purposes, it is more likely that a single snapshot image will be satisfactory, where the exposure duration is short to avoid eye blur through involuntary movements. This is compatible with the use of a LED illumination source that is easily driven to provide a momentary flash of illumination. However, prior to a single image capture, a video image stream may be used to guide an operator to properly set the illuminating geometry.

In other example embodiments, multiple illumination sources may be used for illuminating the eye. For example, rather than use a single discrete source, a distributed source or an aggregation of discrete sources can be used. A single physical setting to the eye could be used and a satisfactory image may be obtained—not by moving the patient or the apparatus around—but either by taking advantage of a distributed source or by electronically activating sources at different positions and angles until certain pre-conditions for obtaining a satisfactory image is met. The distributed source could of course simply be an aggregation of discrete sources. For example, a typical discrete source is a light-emitting diode (LED) which has a typical emitting area measuring 1×1 mm although it may be much smaller. Alternatively, an aggregation of LEDs may be used to increase the total energy launched in a flash or create particular illumination shapes, incident angles and sizes.

The embodiments described herein have at least two significant advantages over conventional imaging techniques. The use of light in the NIR region of the spectrum, typically from a LED source, allows for efficient access to the choroidal layer as the intermediate absorption is much less, permitting a better quality of the resulting image. The use of electronic image sensors lends itself to advanced digital light processing techniques that further enhances the image through contrast enhancement, for example. In addition, there is no requirement for the illumination source path to be directly in contact with the patient as it is sufficient to allow the illuminating light to pass through the air before impinging on or near the eye of the patient. This arrangement removes concerns regarding hygiene and allergies to materials.

The choroidal images can be used for an initial observation and for comparing images taken at different time intervals to identify changes in the choroid over time. As mentioned earlier, images of the choroid may aid in the detection of ocular diseases such as choroidal melanoma and choroidal neovascularisation. In addition, the ability to monitor new vessels developing in the choroid would be significant for tracking ocular health. Current techniques do not readily detect certain cases of occult neovascularisation and can easily be missed. Early detection of any adverse development in the choroid can lead to immediate treatment with anti-VEGF drugs and lessen the damage to the retina from physical disruption and leaking vessels.

In an embodiment, the choroidal imaging technique described herein is also used to measure blood oxygenation levels. In this embodiment, choroidal images are captured using at least two illuminating wavelengths on either side of the oxygen isobestic wavelength near 815 nm. The images may be captured with two or more image sensors simultaneously or in time sequence. The relative brightness at any location in the images provides an indication of the oxygenation level.

The choroidal images obtained at different time intervals can be registered to identify disease progression, for example. A method for performing registration of multispectral images using cross-over points and bifurcation points of blood vessel in an eye is described in commonly owned PCT Application CA2011/050038 entitled "Registration Method for Multispectral Retinal Images," the contents of which are incorporated by reference in their entirety herein.

A method for quantifying disease progression through retinal health assessment and management is described in commonly owned PCT Application entitled "Method and System for Retinal Health Management," the contents of which are incorporated by reference in their entirety herein.

A method and apparatus for imaging the choroid has been described herein. An advantage of the method and apparatus according to embodiments described herein is that any part of the choroid that can be observed via the pupil can be imaged. The illumination optics and the collection optics are different and the illumination and collection is not performed through the same aperture. Consequently, a wide area around the posterior pole can be viewed or imaged with even illumination. Another advantage of the method and apparatus described herein over conventional methods is the ability to image right through the choroid. Current optical coherence tomography (OCT) based methods only seem to view the inner layers, while the method and apparatus described herein aids in the visualization of the deeper Haller and Sattler layers of larger choroidal vessels.

The above-described embodiments are intended to be examples only. Alterations, modifications and variations can be effected to the particular embodiments by those of skill in the art without departing from the scope, which is defined solely by the claims appended hereto.

What is claimed is:

1. A method to image the choroid of an eye, the method comprising:
    transclerally illuminating the choroid by propagating a substantial portion of incident light through the sclera of the eye, the incident light having a wavelength spectrum in the near-infrared region and the sclera acting as a waveguide to guide, substantially through total internal reflection, the incident light to illuminate the choroid from the rear of the eye; and
    obtaining a transmission image of the choroid by collecting the light passing out through the choroid and the pupil of the eye using an image sensor.

2. The method of claim 1, wherein transclerally illuminating the choroid comprises applying the incident light transdermally through the upper or lower eyelid.

3. The method of claim 1, wherein transclerally illuminating the choroid comprises illuminating the choroid by applying the incident light at a plurality of locations surrounding the eye using one or more light sources associated with different angles of incidence.

4. The method of claim 1, further comprising:
    adjusting the incident angle of the incident light to control the proportion of the incident light that propagates through the sclera to the rear of the eye to the incident light that is transmitted through the sclera near the front of the eye.

5. The method of claim 1, wherein obtaining the image of the choroid comprises capturing a single image of the choroid or capturing a continuous stream of images of the choroid.

6. The method of claim 1, wherein obtaining the image of the choroid comprises capturing an image of the Haller or Sattler layers of larger choroidal vessels.

7. The method of claim 1, further comprising:
    providing an additional light source having a wavelength spectrum in the visible region for identifying the illumination region of the incident light having the wavelength spectrum in the near-infrared region.

8. The method of claim 1, further comprising:
    adjusting at least one of size, shape, orientation and convergence angle of the incident light to minimize interference from unwanted scattering.

9. The method of claim 1, further comprising:
    measuring blood oxygenation level using at least two images obtained at different wavelengths on either side of the oxygen isobestic wavelength in the near-infrared region.

10. An apparatus for imaging the choroid of an eye, the apparatus comprising:
    an illumination source for transclerally illuminating the choroid by propagating a substantial portion of incident light through the sclera of the eye, the incident light having a wavelength spectrum in the near-infrared region and the sclera acting as a waveguide to guide, substantially through total internal reflection, the incident light to illuminate the choroid from the rear of the eye; and
    an image sensor for collecting the light passing out through the choroid and the pupil of the eye to obtain a transmission image of the choroid.

11. The apparatus of claim 10, wherein the illumination source includes means to illuminate the choroid through a plurality of locations surrounding the eye.

12. The apparatus of claim 10, wherein the illumination source includes one or more light emitting diodes (LEDs) emitting light in one or more wavelengths in the near-infrared region.

13. The apparatus of claim 10, wherein the illumination source is a single discrete source.

14. The apparatus of claim 10, wherein the illumination source is a distributed source or an aggregation of discrete sources.

15. The apparatus of claim 10, further comprising:
    means to capture a single image of the choroid or means to capture the choroidal images in a continuous stream of images of the choroid.

16. The apparatus of claim 10, further comprising:
    an optical fibre to deliver the incident light having a wavelength spectrum in the near-infrared region.

17. The apparatus of claim 10, further comprising:
    an additional light source having a wavelength spectrum in the visible region for identifying the illumination region of the incident light having the wavelength spectrum in the near-infrared region.

* * * * *